United States Patent
Lee et al.

(10) Patent No.: US 9,591,963 B2
(45) Date of Patent: Mar. 14, 2017

(54) ENDOSCOPE BENDING MODULE MANUFACTURING METHOD

(71) Applicant: Samsung Electronics Co., Ltd., Gyeonggi-do (KR)

(72) Inventors: Jin-won Lee, Gyeonggi-do (KR); Mun-kue Park, Gyeonggi-do (KR); Su-Kwang Lim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 386 days.

(21) Appl. No.: 14/368,223

(22) PCT Filed: Dec. 18, 2012

(86) PCT No.: PCT/KR2012/011073
§ 371 (c)(1),
(2) Date: Jun. 23, 2014

(87) PCT Pub. No.: WO2013/094965
PCT Pub. Date: Jun. 27, 2013

(65) Prior Publication Data
US 2014/0378767 A1    Dec. 25, 2014

(30) Foreign Application Priority Data

Dec. 23, 2011   (KR) .................. 10-2011-0141598

(51) Int. Cl.
*A61B 1/005*   (2006.01)
*A61B 1/008*   (2006.01)
*A61B 1/00*    (2006.01)

(52) U.S. Cl.
CPC ............ *A61B 1/0055* (2013.01); *A61B 1/005* (2013.01); *A61B 1/008* (2013.01); *A61B 1/0011* (2013.01);
(Continued)

(58) Field of Classification Search
CPC ............ A61B 1/00064; A61B 1/00105; A61B 1/0011; A61B 1/005; A61B 1/0055;
(Continued)

(56) References Cited

U.S. PATENT DOCUMENTS

| 2009/0093679 A1 | 4/2009 | Suigetsu et al. |
| 2010/0056868 A1* | 3/2010 | Kitagawa ........... G02B 23/2407 600/142 |

(Continued)

FOREIGN PATENT DOCUMENTS

| JP | 2000023908 | 1/2000 |
| JP | 2008259634 | 10/2008 |

(Continued)

OTHER PUBLICATIONS

PCT/ISA/210, Search Report issued on PCT/KR2012/011073, (pp. 2).

*Primary Examiner* — Jermie Cozart
(74) *Attorney, Agent, or Firm* — The Farrell Law Firm, P.C.

(57) ABSTRACT

Provided is a manufacturing method of a bending module that forms a plurality of joint members by press-processing sheet material, with each joint member having a joint member body, a connection protrusion and a wire guide protrusion having a wire guide hole formed at one side corner of the joint member body, and one connection protrusion is formed at another side corner of the joint member body. The wire guide protrusions are folded with respect to the joint member bodies; a joint member assembly is formed by arranging the plurality of joint members in parallel and connecting neighboring connection members to connect the joint members together; the joint member assembly are bent to a ring shape; and each joint member is connect to each other by welding corners thereof.

7 Claims, 16 Drawing Sheets

(52) U.S. Cl.
CPC ........ *A61B 1/0057* (2013.01); *A61B 1/00064* (2013.01); *A61B 1/00105* (2013.01); *A61B 1/00128* (2013.01); *Y10T 29/49924* (2015.01); *Y10T 29/49956* (2015.01); *Y10T 29/49968* (2015.01)

(58) Field of Classification Search
CPC ........... A61B 1/00128; Y10T 29/49943; Y10T 29/49956; Y10T 29/49968; Y10T 29/49941; Y10T 29/49924; Y10T 29/49922; Y10T 29/49936; Y10T 29/49593
See application file for complete search history.

(56) References Cited

U.S. PATENT DOCUMENTS

| | | | | |
|---|---|---|---|---|
| 2010/0076267 A1* | 3/2010 | Sugisawa | ............. | A61B 1/0055 600/146 |
| 2010/0116081 A1* | 5/2010 | Pistor | .................... | A61B 1/0055 74/490.05 |
| 2011/0313251 A1* | 12/2011 | Kitagawa | ............. | A61B 1/0055 600/142 |
| 2012/0170970 A1* | 7/2012 | Kitagawa | ............. | A61B 1/0011 403/81 |

FOREIGN PATENT DOCUMENTS

| | | |
|---|---|---|
| JP | 2010259479 | 11/2010 |
| JP | 2011067423 | 4/2011 |
| JP | 2011156269 | 8/2011 |

\* cited by examiner

ENDOSCOPE BENDING MODULE MANUFACTURING METHOD

PRIORITY

This application is a National Stage of International Application No. PCT/KR2012/011073, filed on Dec. 18, 2012, and claims priority to Korean Patent Application No. 10-2011-0141598 filed on Dec. 23, 2011, the entire disclosure of each of which is incorporated herein by reference.

FIELD OF THE INVENTION

Methods and apparatuses consistent with exemplary embodiments relate to a bending module provided in endoscope equipment and a manufacturing method thereof, and more particularly, to a bending module which can reduce a manufacturing cost, and a manufacturing method thereof.

BACKGROUND OF THE INVENTION

The endoscope is equipment for examining the interior of an examinee's body that is difficult to observe with naked eyes, and is widely used in the medical field.

The endoscope generally includes an insertion part which is inserted into the interior of the examinee's body and includes a photographing module, a manipulator which is manipulated by a user to drive the photographing module, and a monitor which displays a photographed image. The insertion part generally includes an insertion tube connected to the manipulator, the photographing module to photograph the interior of the examinee's body, and a bending module to connect the insertion tube and the photographing module to each other. The bending module is pitch or yaw-driven by the user, thereby facilitating accuracy of approach of the photographing module in relation to a part to be examined.

The endoscope is relatively expensive, and a need exists for production at low cost considering an increasing demand for the endoscope equipment. The above-described bending module is one of the expensive parts of the endoscope and thus there is a need for a method for reducing a manufacturing cost of the bending module in order to produce the endoscope at low cost.

SUMMARY

One or more exemplary embodiments provide a bending module for endoscope equipment, which can reduce a manufacturing cost and a manufacturing method thereof.

According to an aspect of an exemplary embodiment, there is provided a method for manufacturing a bending module, the method including forming a plurality of joint members by press-processing a sheet material, wherein each joint member includes a joint member body, a plurality of wire guide protrusions each having a wire guide hole formed on a side edge of the joint member body, a first connection protrusion formed on the side edge of the joint member, and a second connection protrusion formed on an other side edge of the joint member body; folding each of the plurality of wire guide protrusions with respect to the joint member body; forming a joint member assembly by arranging the plurality of joint members in parallel and connecting adjacent joint members via respective connection protrusions; bending the joint member assembly such that each of the plurality of joint members has a ring shape; and connecting opposite ends of each of the plurality of joint members to each other by welding.

Forming the joint members may include forming the wire guide holes by a drawing process such that the wire guide hole has a depth greater than a thickness of the sheet material.

The drawing process may be integrated into the pressing process of the sheet material and may be applied.

The method may further include, after forming the joint members, processing the wire guide holes such that an exit part of the wire guide hole has a chamfered shape.

Forming the joint members may be performed by a single pressing process.

Forming the joint member assembly may include rivet-connecting the connection protrusions of the two neighboring joint members.

Forming the joint members may include forming two wire guide protrusions and first and second connection protrusions on one side edge of the joint member body, and forming third and fourth connection protrusions on the other side edge of the joint member body.

According to an aspect of another exemplary embodiment, there is provided a method for manufacturing a bending module, the method including forming a plurality of joint members by press-processing a sheet material, wherein each joint member includes a joint member body, at least one connection protrusion and at least one wire guide protrusion having a wire guide hole are formed on one side edge of the joint member body, and at least one connection protrusion is formed on the other side edge of the joint member body; folding the wire guide protrusions with respect to the joint member body; roll-bending the joint members to have a ring shape; connecting opposite ends of each of the joint members to each other by welding; and forming a joint member assembly by arranging the plurality of joint members in parallel and connecting the connection protrusions of the two neighboring joint members such that the plurality of joint members are connected to one another.

According to an aspect of another exemplary embodiment, there is provided a bending module for an endoscope, the bending module including a joint ring assembly in which a plurality of joint rings are connected to one another, wherein each of the joint rings includes a joint ring body of a ring shape with at least one wire guide protrusion formed on a side edge of the joint ring body and having a wire guide hole, and wherein the wire guide hole has a depth greater than a thickness of the joint ring body.

The wire guide hole may include an entrance part tapering toward an inside of the wire guide hole.

The entrance part may have a rounded shape.

The wire guide hole may include an exit part tapering toward an inside of the wire guide hole.

The exit part may have a chamfered shape.

Each of the wire guide protrusions may be integrally formed with the joint ring body.

At least one connection protrusion including a joint connection hole may be formed on each of one side edge and the other side edge of the joint ring body.

Two wire guide protrusions and first and second connection protrusions may be formed on one side edge of the joint ring body, and third and fourth connection protrusions may be formed on the other side edge of the joint ring body.

The first and second connection protrusions of a certain joint ring may make a pair with the third and fourth connection protrusions of another neighboring joint ring, and may be rivet-connected to each other.

The plurality of joint rings may have a common shape, and two neighboring joint rings may have a phase difference of 90° to each other in a direction of rotation of the joint rings about a common center line.

According to an aspect of another exemplary embodiment, there is provided endoscope equipment including the above-described bending module.

BRIEF DESCRIPTION OF THE DRAWINGS

The above and/or other aspects of the invention will become and more readily appreciated from the following description of the exemplary embodiments, taken in conjunction with the accompanying drawings of which.

DETAILED DESCRIPTION OF EXEMPLARY EMBODIMENTS OF THE INVENTION

Figure 1:
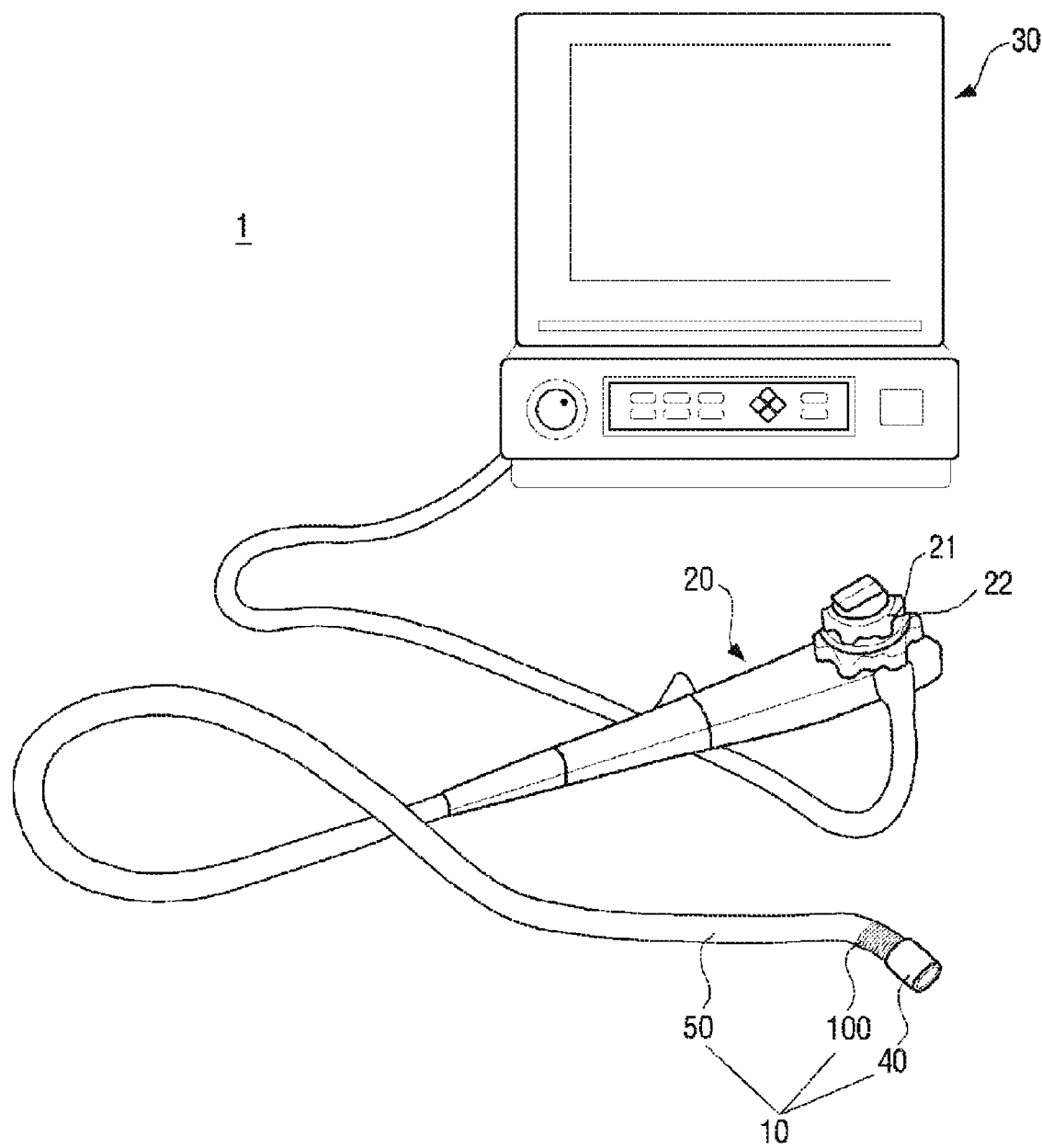
FIG. 1 is a perspective view schematically illustrating an example of endoscope equipment according to an exemplary embodiment.

Reference will now be made in detail to the present exemplary embodiments of the present invention, examples of which are illustrated in the accompanying drawings, wherein like reference numerals refer to the like elements throughout. The exemplary embodiments are described below in order to explain the present invention by referring to the figures.

FIG. 1 is a perspective view schematically illustrating an example of endoscope equipment according to an exemplary embodiment, The endoscope equipment 1 of FIG. 1 is a medical endoscope for examining human organs such as large intestines, and is merely an example of endoscope equipment to which the present disclosure is applicable. The present disclosure can be applied to different kinds of endoscope equipment, e.g., industrial endoscope equipment.

Referring to FIG. 1, the endoscope equipment 1 includes an insertion part 10 which is inserted into of an examinee's body to view an interior thereof, e.g., to view human organs, a manipulator 20 which is gripped and manipulated by a user, and a monitor 30 which displays an image of a part to be examined.

The insertion part 10 includes a photographing module 40 disposed at a free end thereof, an insertion tube 50 extending from the manipulator 20, and a bending module 100 to connect the photographing module 40 and the insertion tube 50 to each other.

The photographing module 40 has parts such as a small camera, a light source, etc., mounted therein to photograph the part being examined. The insertion tube 50 is made of a flexible material so that the insertion tube 50 can move along the shape of the examinee's body, and accommodates electric cables necessary for operating the photographing module 40 and driving wires necessary for driving the bending module 100. In addition, the bending module 100 is pitch or yaw-driven by user's manipulation, thereby helping the photographing module 40 exactly approach a target part to be photographed.

The manipulator 20 includes a vertical manipulation knob 21 and a horizontal manipulation knob 22. As the user manipulates the manipulation knobs 21 and 22, the bending module 100 is driven in respective pitch and yaw directions via driving wires accommodated in the insertion tube 50.

The monitor 30 displays an image photographed by the photographing module 40 so that the user can observe the state of the examined part.

Hereinafter, an embodiment of the bending module 100 will be explained in detail with reference to FIGS. 2 to 6.

Figure 2:
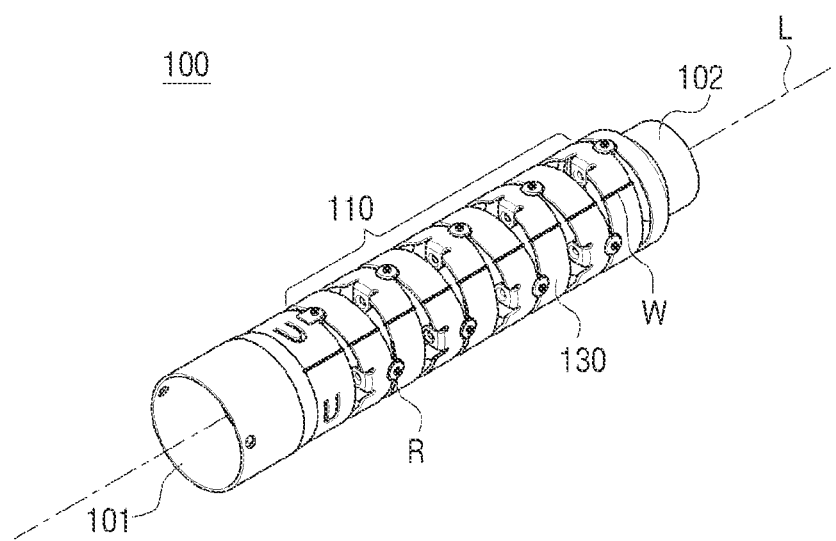
FIG. 2 is an enlarged perspective view of a bending module provided in the endoscope equipment of FIG. 1.
Figure 3:
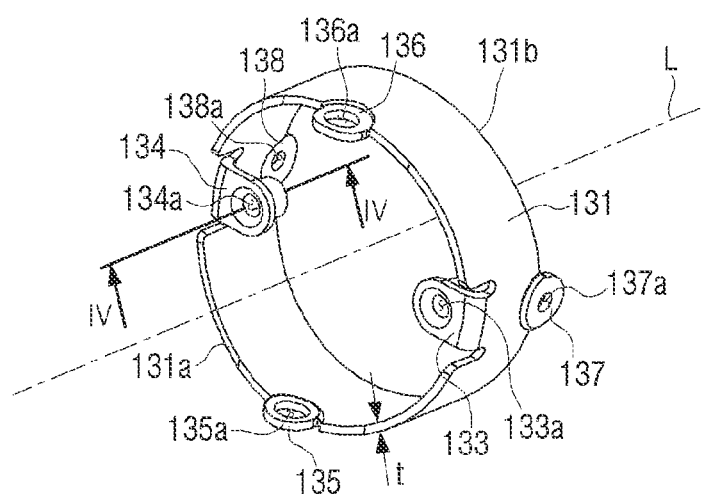
FIG. 3 is a perspective view of a joint ring provided in the bending module of FIG. 2.
Figure 4:
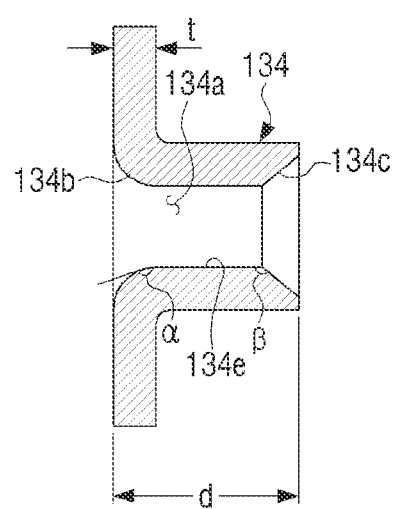
FIG. 4 is a cross section view of a wire guide protrusion of the joint ring of FIG. 3 taken along line IV-IV.
Figure 5:
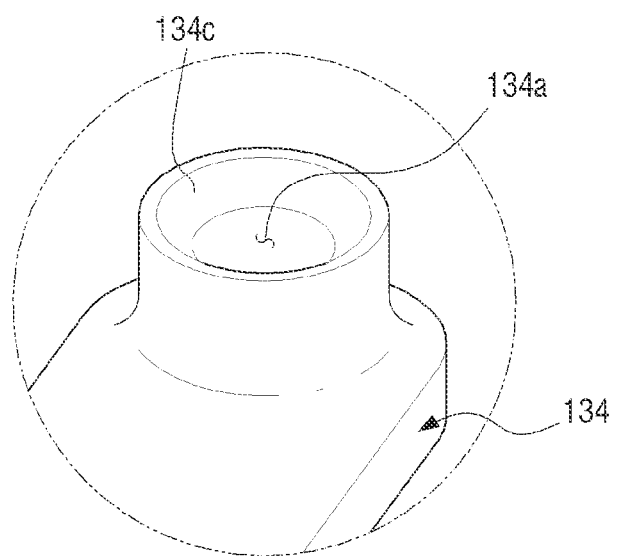
FIG. 5 is a bottom perspective view of the wire guide protrusion of the joint ring of FIG. 3.
Figure 6:
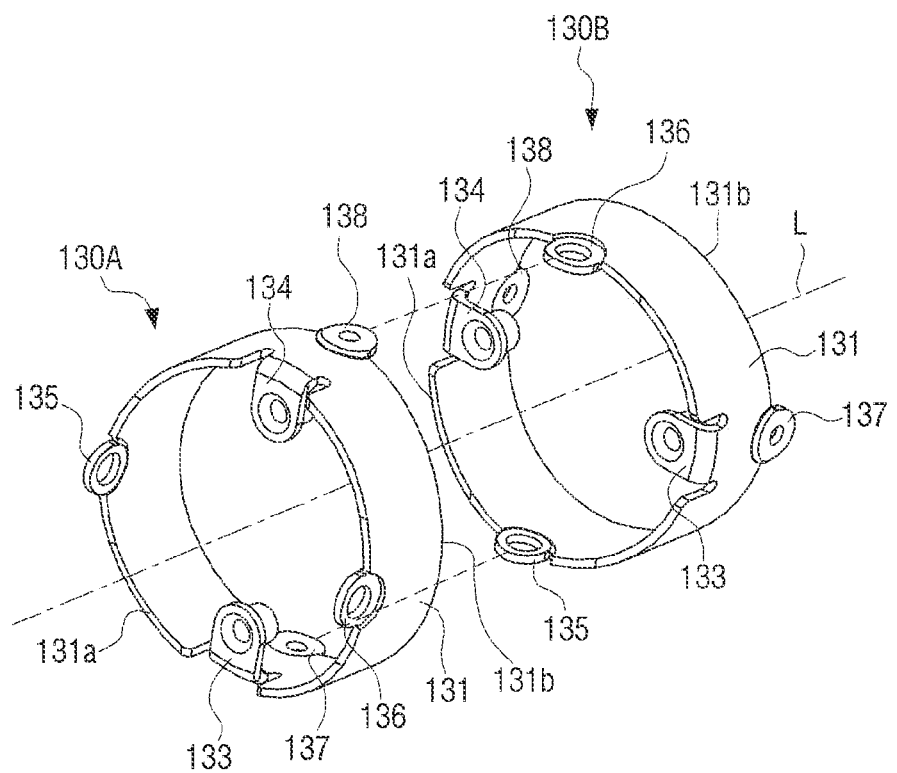
FIG. 6 is a perspective view illustrating two neighboring joint rings provided in the bending module of FIG. 2.

FIG. 2 is an enlarged perspective view of the bending module provided in the endoscope equipment of FIG. 1, FIG. 3 is a perspective view of a joint ring provided in the bending module of FIG. 2, FIG. 4 is a cross section view of a wire guide protrusion of the joint ring of FIG. 3 taken along line IV-IV, FIG. 5 is a bottom perspective view of the wire guide protrusion of the joint ring of FIG. 3, and FIG. 6 is a perspective view illustrating two neighboring joint rings provided in the bending module of FIG. 2.

Referring to FIG. 2, the bending module 100 includes a joint ring assembly 110, a first connection member 101, and a second connection member 102.

The first connection member 101 is configured to connect the above-described insertion tube 50 to one end of the joint ring assembly 110, and the second connection member 102 is configured to connect the above-described photographing module 40 to the other end of the joint ring assembly 110.

The joint ring assembly 110 is an assembly in which a plurality of joint rings 130 are connected to one another along a center line L of the bending module 100. The joint ring assembly 110 is comprised of 8 joint rings 130 in total in the present exemplary embodiment. However, the number of joint rings may vary in other alternative exemplary embodiments. Since the center line L of the bending module 100 corresponds to an axis to align centers of the plurality of joint rings 130, the center line L may be referred to as a 'common center line L' of the joint rings 130.

The joint rings 130 are preferably connected to one another by rivet members R. Accordingly, the joint rings 130 may pivot about a second axis perpendicular to center line L with reference to the rivet members R relative to one another. Such a pivotal movement of the joint rings 130 enables the bending module 100 to be pitch and yaw-driven.

Referring to FIG. 3, each joint ring 130 includes a joint ring body 131 that is bent into a ring shape, two wire guide protrusions 133 and 134 formed on a same side edge 131a of the joint ring body 131, first and second connection protrusions 135 and 136 formed on one side edge 131a of the joint ring body 131, and third and fourth connection protrusions 137 and 138 formed on a side edge 131b of the joint ring body 131 opposite side edge 131a.

The joint ring body 131, the guide protrusions 133 and 134, and the connection protrusions 135, 136, 137, and 138, which constitute the joint ring 130, are formed from a single flat sheet material, a joint member, having a uniform thickness t. As for the sheet material, a metal sheet material, e.g., stainless steel, a resin sheet material, a composite sheet material, etc., may be applied. A manufacturing method of the joint ring 130 will be described below.

Since the joint ring body 131, the wire guide protrusions 133 and 134, and the connection protrusions 135, 136, 137, and 138 are formed from the same basic material, the sheet material, they have the uniform thickness t and also are integrally formed with one another. In particular, since the wire guide protrusions 133 and 134 are formed in a single body with the joint ring body 131 in the present exemplary embodiment, the manufacturing process can be simplified in comparison to a conventional related manufacturing process in which wire guide protrusions are separately formed and attached to a joint ring body, e.g., by a brazing process.

The wire guide protrusions 133 and 134 face each other on the one side edge 131a of the joint ring body 131 and extend from the one side edge 131a toward the common center line L of the joint rings 130. The wire guide protrusions 133 and 134 include wire guide holes 133a and 134a penetrating therethrough in a direction parallel to the common center line L. The wire guide holes 133a and 134a support and guide driving wires (not shown) for driving the bending module 100.

As shown in FIG. 4, a depth d of the wire guide hole 134a is greater than the thickness t of the joint ring body 131. This is achieved by forming the wire guide hole 134a by applying a drawing process rather than a simple punching process. Since the wire guide hole 134a has the great depth d, a contact area between the wire guide hole 134a and the driving wire increases and thus the driving wire can be smoothly guided.

As shown in FIG. 4, the wire guide hole 134a includes an entrance part 134b formed in a rounded shape and tapering toward the inside. Accordingly, a tilt angle α formed between the entrance part 134b (specifically, a tangent line of the entrance part) and an inner wall 134e of the wire guide hole 134a is an obtuse angle. To this end, when the driving wires are moved by user's manipulation, and friction between the driving wires and the wire guide hole 134a is reduced. Such an entrance part 134b of the rounded shape can be formed without a separate additional process when the wire guide hole 134a is formed by the above-described drawing process.

As shown in FIGS. 4 and 5, the wire guide hole 134a includes an exit part 134c formed in a chamfered shape that tapers toward the inside. Accordingly, a taper angle β formed between the exit part 134c and the inner wall 134e of the wire guide hole 134a is an obtuse angle. To this end, when the driving wires are moved by user's manipulation, friction between the driving wires and the wire guide hole 134a is reduced. Such an exit part 134c of the chamfered shape is formed by adding a chamfering process or a barrel polishing process.

According to the exemplary embodiment described above, since the wire guide hole 134a includes the entrance part 134b of the rounded shape and the exit part 134c of the chamfered shape, friction between the driving wires and the wire guide holes 133a and 134a is reduced and thus damage to the driving wires caused by friction is reduced. In addition, malfunction of the driving wires caused by friction can be prevented.

Referring back to FIG. 3, the first and second connection protrusions 135 and 136 formed on the one side edge 131a of the joint ring 130 are disposed to face each other. Accordingly, one wire guide protrusion 133, the first connection protrusion 135, the other wire guide protrusion 134, and the second connection protrusion 136 are arranged in sequence along the one side edge 131a of the joint ring 130. Third and fourth connection protrusions 137 and 138 formed on the other side edge 131b of the joint ring 130 are disposed to face each other and are formed at locations corresponding to the locations of the wire guide protrusions 133 and 134.

The first to fourth connection protrusions 135, 136, 137, and 138 protrude from the joint ring body 131 along the common center line L, and include joint connection holes 135a, 136a, 137a, and 138a to connect the joint rings 130 to one another. As shown in FIG. 3, the first and second connection protrusions 135 and 136 protrude toward the inside of the joint ring 130, whereas the third and fourth connection protrusions 137 and 138 protrude toward the outside of the joint ring 130. The connection protrusions 135 to 137 protrude as much as t/2 or t/3 (wherein t is a thickness of the connection protrusion or thickness of the joint ring body).

Referring to FIG. 6, two neighboring joint rings 130A and 130B have the same shape, but placement of one joint ring corresponds to placement of the other joint ring rotated about the common line L by 90° in a clockwise or counter clockwise direction. For example, when one joint ring 130A is rotated by 90° in the counter clockwise direction, the placement of the joint ring 130A is the same as that of its neighboring joint ring 130B. In other words, the two neighboring joint rings 130A and 130B have a phase difference of 90° therebetween in the direction of the rotation about the common center line L.

Due to such an arrangement of the joint rings 130A and 130B, the locations of the third and fourth connection protrusions 137 and 138 of the joint ring 130A correspond to the locations of the first and second connection protrusions 135 and 136 of the neighboring joint ring 130B. Therefore, the third connection protrusion 137 of the joint ring 130A may be rivet-connected with the first connection protrusion 135 of adjacent joint ring 130B. In addition, the fourth connection protrusion 138 of the joint ring 130A may be rivet-connected with the second connection protrusion 136 of adjacent joint ring 130B. The plurality of joint rings 130 constituting the bending module 100 in the present exemplary embodiment are connected to one another in the same way as the above-described two joint rings 130A and 130B are connected to each other.

Hereinafter, two exemplary embodiments of a method for manufacturing the above-described bending module 100 will be explained.

Hereinafter, a method for manufacturing a bending module according to a first exemplary embodiment will be explained with reference to FIGS. 7 to 14.

Figure 7:
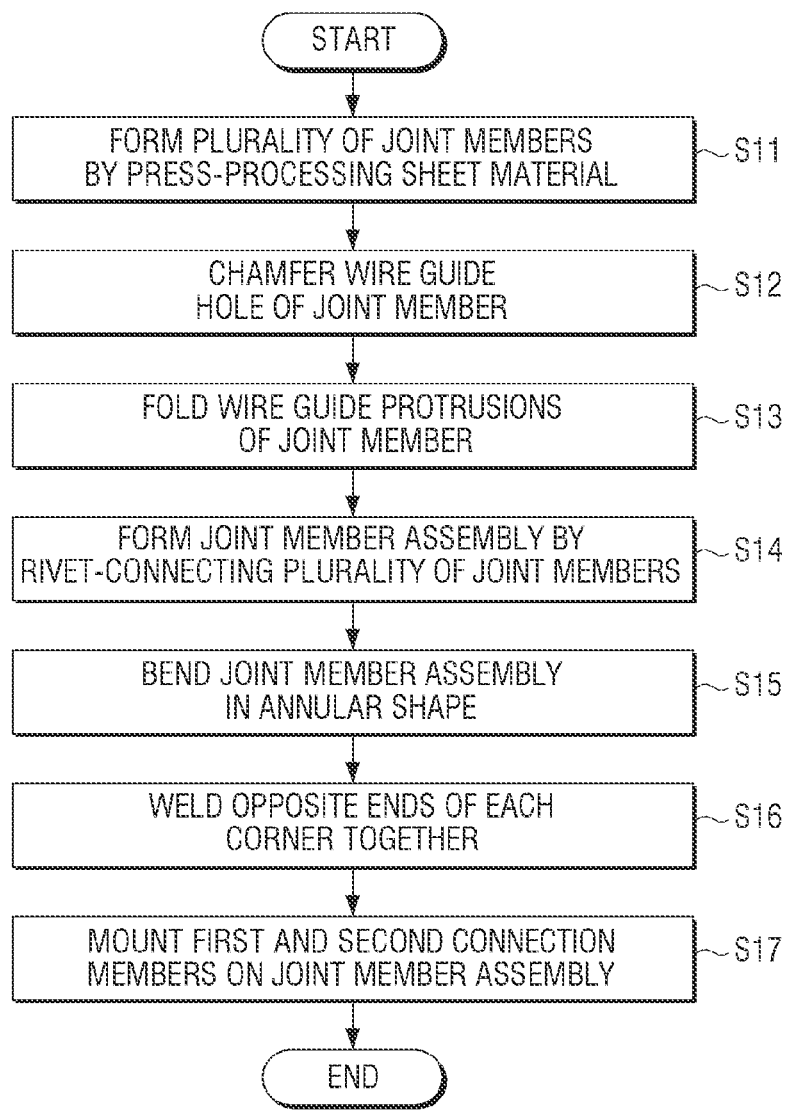
FIG. 7 is a flowchart illustrating a method for manufacturing a bending module according to a first exemplary embodiment.
Figure 8:
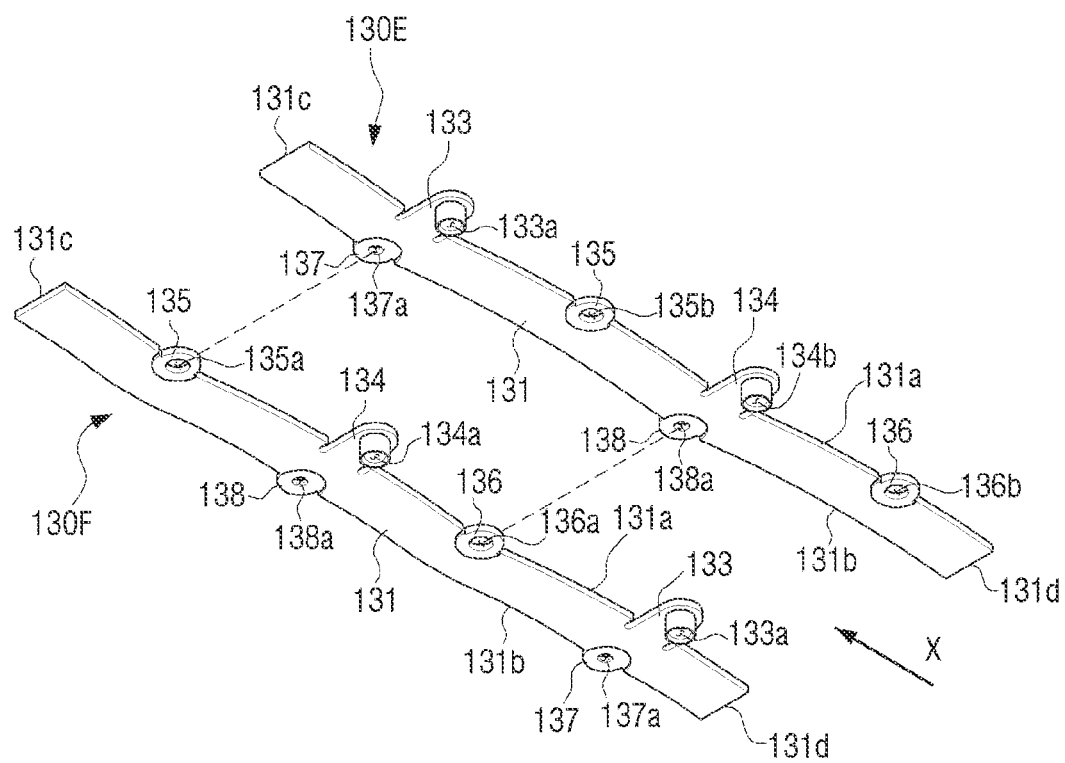
FIG. 8 is a perspective view illustrating joint members being formed according to the method of FIG. 7.
Figure 9:
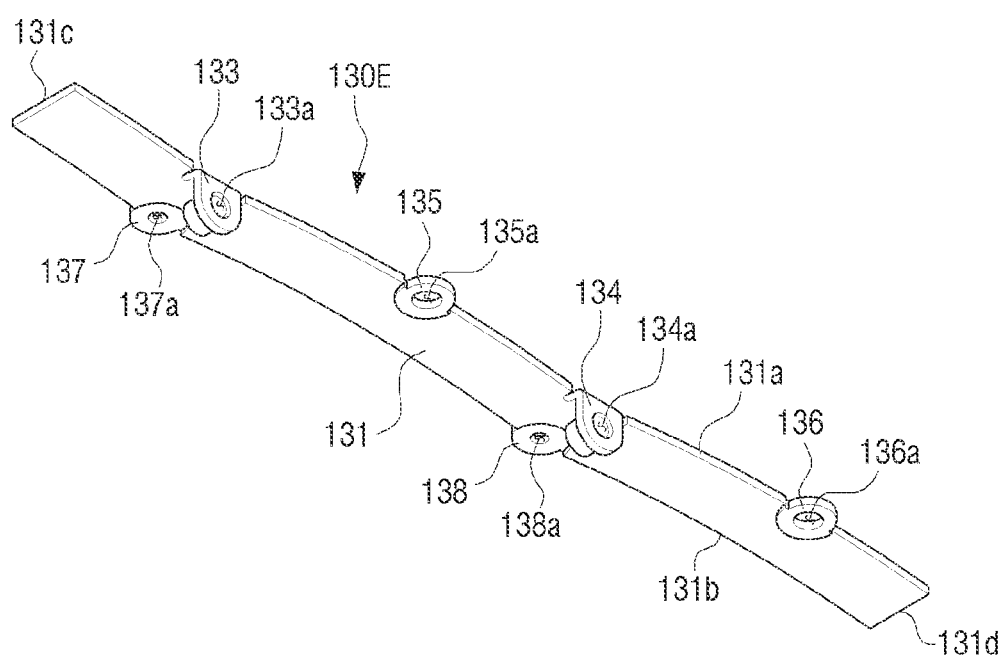
FIG. 9 is a perspective view showing a folding operation of the method of FIG. 7.
Figure 10:
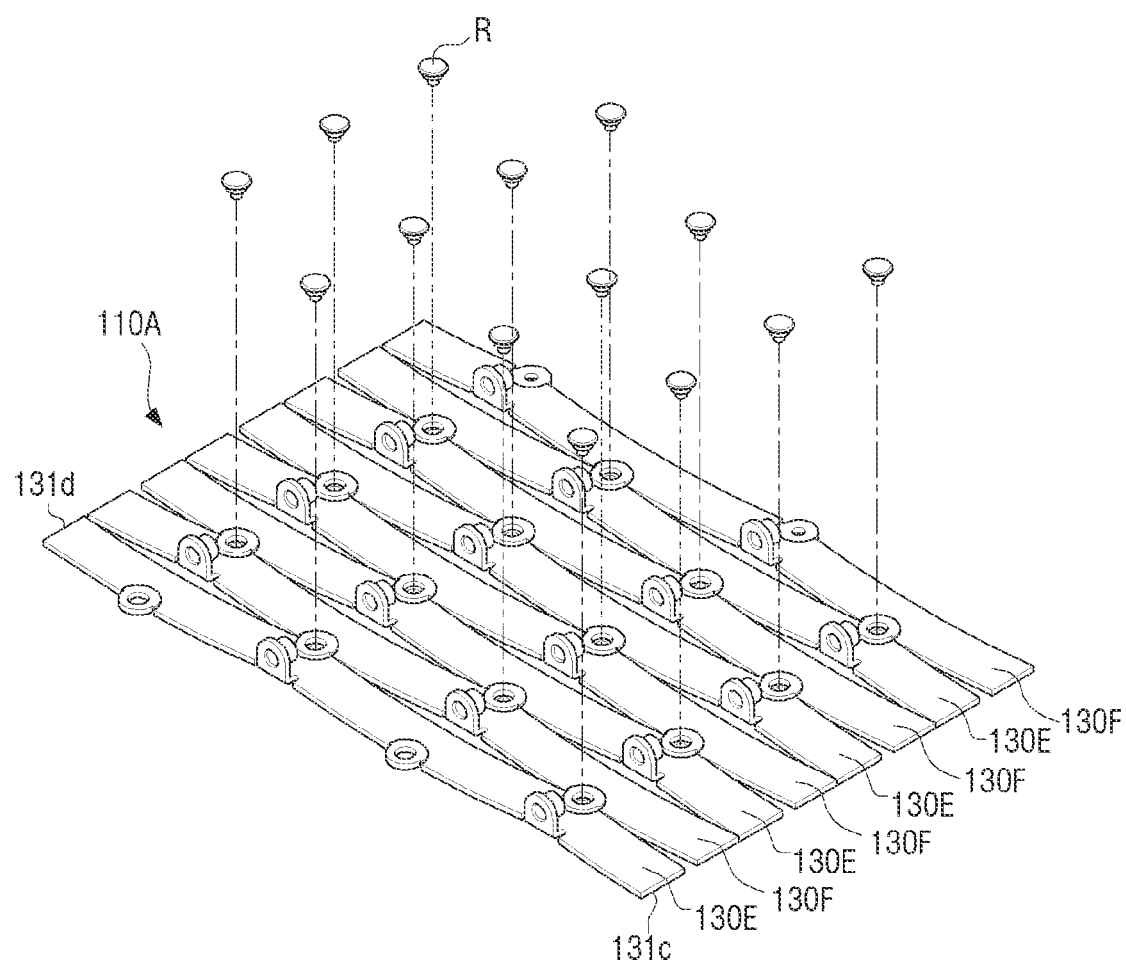
FIG. 10 is a perspective view illustrating a joint member assembly forming operation of the method of FIG. 7.
Figure 11:
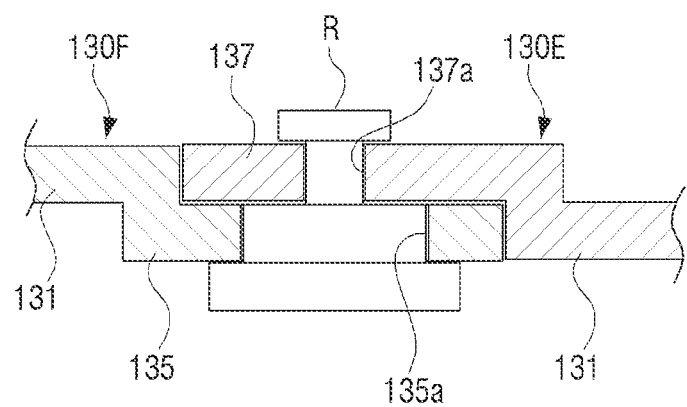
FIG. 11 is a cross section view illustrating two wire guide protrusions which are rivet-connected to each other.
Figure 12:
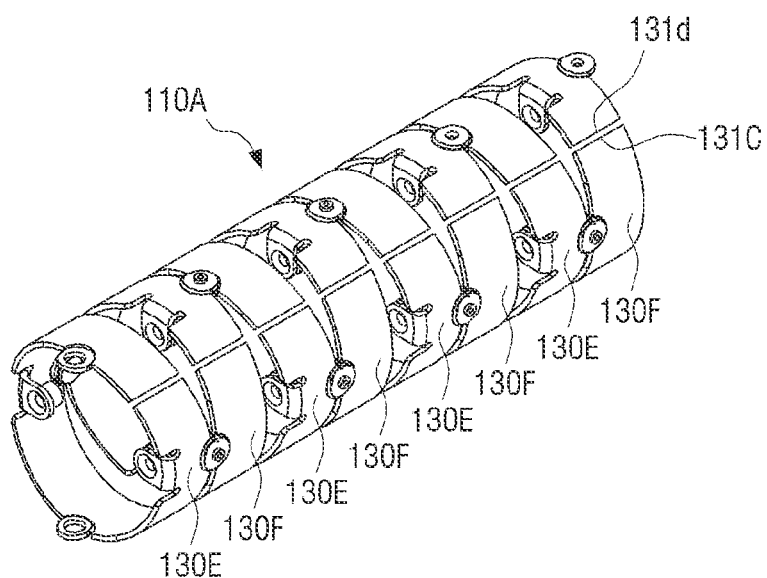
FIG. 12 is a perspective view illustrating an output of a bending operation of the method of FIG. 7.
Figure 13:
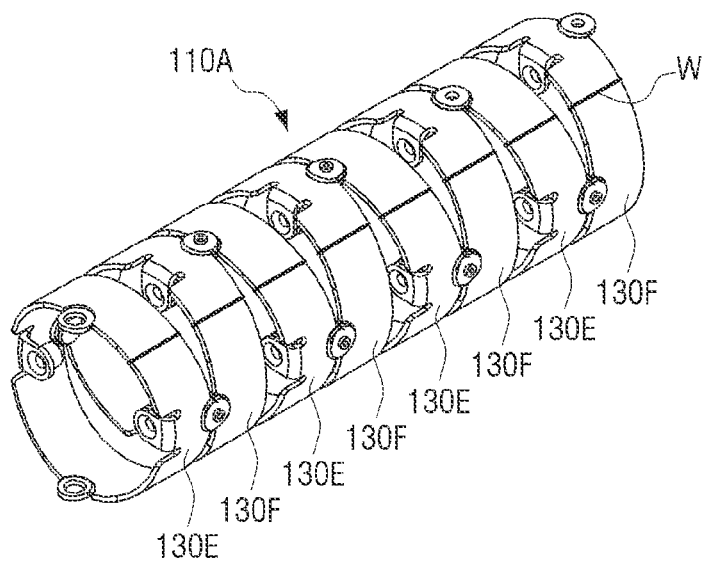
FIG. 13 is a perspective view illustrating an output of a welding operation of the method of FIG. 7.
Figure 14:
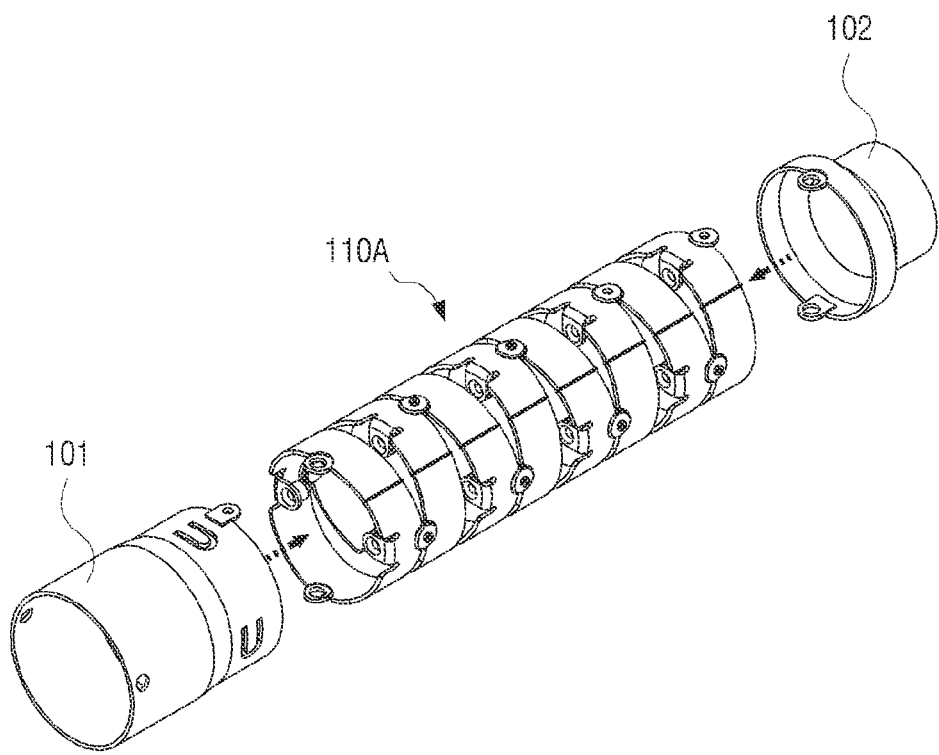
FIG. 14 is a perspective view illustrating a connection member mounting operation of the method of FIG. 7.

FIG. 7 is a flowchart illustrating a method for manufacturing a bending module according to a first exemplary embodiment, FIG. 8 is a perspective view illustrating joint members being formed according to the method of FIG. 7, FIG. 9 is a perspective view illustrating a folding operation of the method of FIG. 7, FIG. 10 is a perspective view illustrating a joint member assembly forming operation of the method of FIG. 7, FIG. 11 is a cross section view illustrating two wire guide protrusions rivet-connected with each other, FIG. 12 is a perspective view illustrating an output of a bending operation of the method of FIG. 7, FIG. 13 is a perspective view illustrating a an output of welding operation of the method of FIG. 7, and FIG. 14 is a perspective view illustrating a connection member mounting operation of the method of FIG. 7.

Referring to FIG. 7, a plurality of joint members for forming a joint ring is formed by press-processing a flat sheet material having a predetermined thickness t (Step S11).

As shown in FIG. 8, the joint members formed in step S11 are divided into a first type of joint member 130E and a second type of joint member 130F. Features that are common to the first type of joint member 130E and the second type of joint member 130F are that the joint members 130E and 130F include a substantially rectangular joint member body 131, and include two wire guide protrusions 133 and 134, and first and second connection protrusions 135 and 136 formed on one side edge 131a of the joint member body 131, with third and fourth connection protrusions 137 and 138 formed on the other side edge 131b of the joint member body 131.

However, the guide protrusions and connection protrusions of each type of joint member are shifted in a lengthwise direction from corresponding locations of the guide protrusions and connection protrusions of the other type of joint member. The shift between positions of each type of joint member body is in the X direction shown in FIG. 8, i.e., a pitch P between the guide protrusion and the connection protrusion. The pitch P corresponds to about ¼ of the length of the joint member body 131. For example, the wire guide protrusion 134 of the first type of joint member 130E is formed at a location corresponding to the location of the wire guide protrusion 134 of the second type joint member 130F shifted in the direction of X as much as the pitch P. In addition, the second connection protrusion 136 of the second type of joint member 130E is formed at a location corresponding to the location of the second connection protrusion 136 of the first type joint member 130F shifted in the direction of X as much as the pitch P.

The operation (Step S11) of forming the joint members 130E and 130F does not exclude a combination of stepwise pressing processes, but may be performed by a single pressing process. As described above with reference to FIG. 4, the wire guide hole 134a is formed by applying a drawing process such that the wire guide hole 134a has a depth 'd' greater than a thickness 't' of the sheet material and also has a rounded entrance part 134b, and the drawing process applied to the operation of forming the wire guide hole 134a can be integrated into the pressing process for forming the joint members.

Since the joint members 130E and 130F for forming the joint ring are formed by press-processing the flat sheet material in the present exemplary embodiment, the manufacturing process is simple in comparison to the related-art method in which a joint ring is formed by slicing a cylindrical basic material, and thus the manufacturing cost can be reduced. In particular, since the wire protrusions 133 and 134 are formed concurrently with the joint member body 131 by the pressing process, the manufacturing cost can be further reduced in comparison to conventional methods in which wire guide protrusions are separately formed and are attached in a subsequent process, e.g., by a brazing process.

Next, the wire guide holes 133a and 134a of the wire guide protrusions 133 and 134 are chamfered to have a chamfered shape (see 134c of FIG. 4) (Step S12), and the chamfering process may be substituted with other processes such as a barrel polishing process.

Next, as shown in FIG. 9, the wire guide protrusions 133 and 134 are folded to be substantially perpendicular to the joint member body 131 (Step S13).

Next, as shown in FIG. 10, a joint member assembly 110A is formed by arranging the plurality of joint members 130E and 130F in parallel and then rivet-connecting adjacent joint members (Step S14). In this case, the first type of joint member 130E and the second type of joint member 130F are arranged alternately. In addition, the first and second connection protrusions 135 and 136 of a certain joint member (see FIG. 8) make a pair with the third and fourth connection protrusions 137 and 138 of another neighboring joint member (see FIG. 8) and are rivet-connected to each other.

For example, referring to FIG. 11, adjacent joint members 130E and 130F are rivet-connected with each other by placing the third connection protrusion 137 of the first type of joint member 130E and the first connection protrusion 135 of the second type of joint member 130F to overlap each other, and inserting a rivet member R into the joint connection holes 137a and 135a of the connection protrusions 137 and 135.

Next, the joint member assembly 110A is bent using a substantially cylindrical bending jig (not shown) in a shape corresponding to the jig (Step S15). Then, the joint members 130E and 130F finally have a ring shape as shown in FIG. 12. In this case, opposite ends 131c and 131d of each of the joint members 130E and 130F face each other with a minute gap therebetween.

Next, the opposite ends 131c and 131d of each of the joint members 130E and 103F are connected with each other by welding (for example, laser welding) (Step S16). Then, each of the joint members 130E and 130F has a complete ring shape having a welding line W as shown in FIG. 13, and the joint member assembly 110A is completely identical to the joint ring assembly 110 shown in FIG. 2.

In Step S17, as shown FIG. 14, the bending module 100 is completely formed by mounting the first connection member 101 for connecting the insertion tube on one end of the joint member assembly 110A by a rivet, and mounting the second connection member 102 for connecting the photographing module on the other end of the joint member assembly 110A by a rivet.

According to the bending module manufacturing method described above, the number of processes can be considerably reduced in comparison with the related-art bending module manufacturing methods. Accordingly, this method can contribute to reducing the manufacturing cost of the bending module and thus contribute to reducing the manufacturing cost of the endoscope equipment. In particular, since this method forms the joint members by pressing the sheet material, the number of processes can be greatly reduced in comparison with the related-art method in which the joint rings are formed by slicing a cylindrical basic material.

Hereinafter, a method for manufacturing a bending module according to a second exemplary embodiment will be explained with reference to FIGS. 15 and 16.

Figure 15:
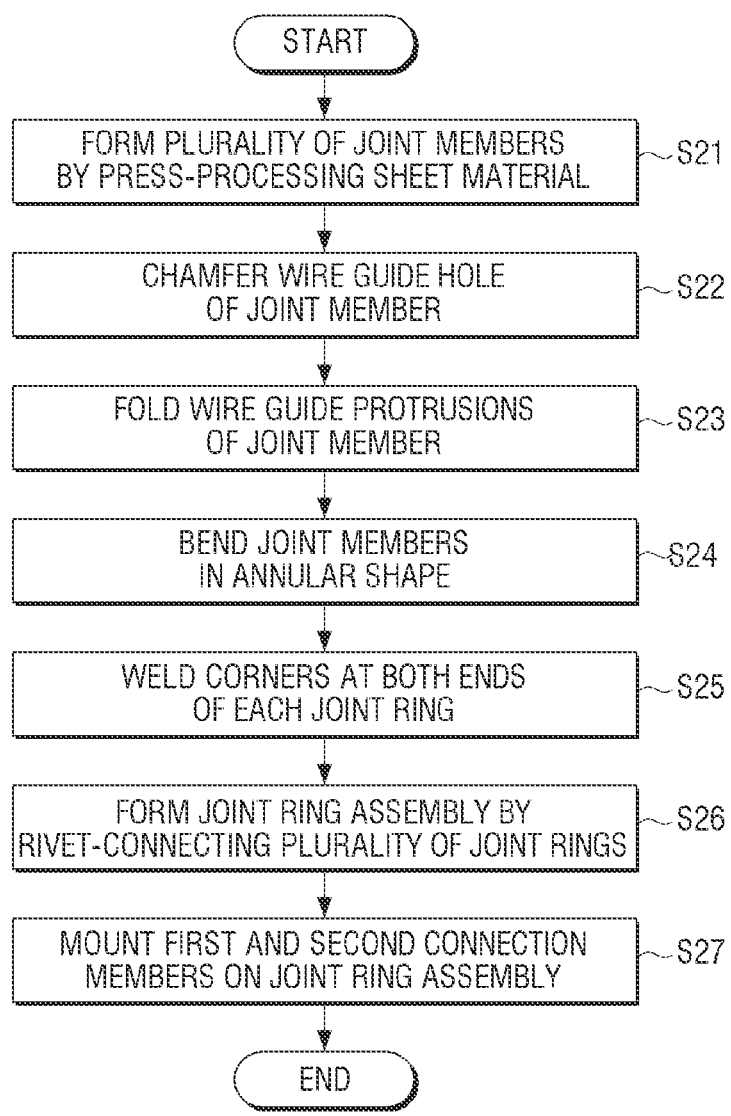
FIG. 15 is a flowchart illustrating a method for manufacturing a bending module according to a second exemplary embodiment.
Figure 16:
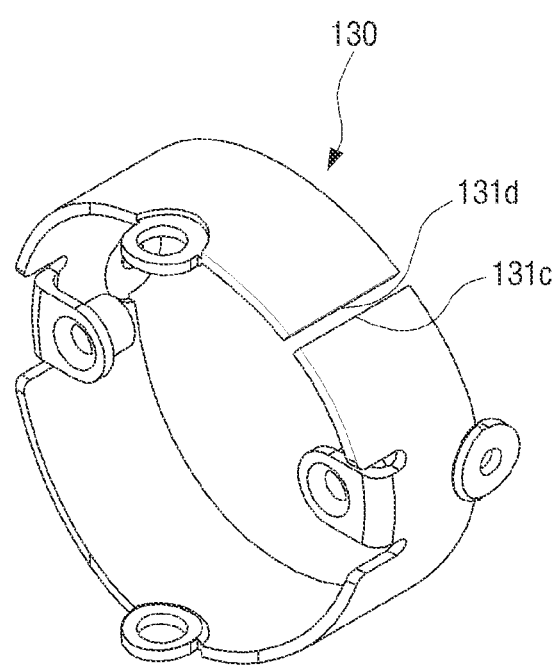
FIG. 16 is a perspective view illustrating a joint member after a bending operation of the manufacturing method of FIG. 15.

FIG. 15 is a flowchart illustrating a method for manufacturing a bending module according to a second exemplary embodiment, and FIG. 16 is a perspective view illustrating a joint member after a bending operation of the manufacturing method of FIG. 15.

Referring to FIG. 15, the method performs operations of forming a plurality of joint members for forming joint rings by pressing a sheet material (Step S21), chamfering wire guide holes of the joint members (Step S22), and folding wire guide protrusions to be perpendicular to a joint member body (Step S23) in sequence. The Steps S21-S23 are completely identical to Steps S11-S13 of the above-described manufacturing method FIG. 7).

Next, each of the joint members 130 is bent in a ring shape as shown in FIG. 16 (Step 24).

Next, opposite ends 131*c* and 131*d* of each of the joint members 130 facing each other are welded to each other (for example, by laser welding) (Step S25).

Next, the plurality of joint rings (joint members) 130 are connected to one another by rivets (Step S26). Then, the joint ring assembly 110A is obtained as shown in FIG. 12. In a similar way to Step 14 (FIG. 7), first and second connection protrusions of a certain joint ring make a pair with third and fourth connection protrusions of another neighboring joint ring and are rivet-connected to each other in step S26.

Finally, the first and second connection members 101 and 102 (see FIG. 14) are mounted on opposite ends of the joint member assembly 110A (Step 27), with Step S27 being the same as Step S17 of FIG. 7.

Like the above-described bending module manufacturing method illustrated in FIG. 7, the bending module manufacturing method illustrated in FIG. 15 can contribute reducing the manufacturing cost of the bending module and accordingly can contribute reducing the manufacturing cost of the endoscope equipment.

The foregoing exemplary embodiments and advantages are merely exemplary and are not to be construed as limiting the present inventive concept. The exemplary embodiments can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method for manufacturing a bending module, the method comprising:

forming a plurality of joint members by press-processing a sheet material, wherein each joint member of the plurality of joint members comprises a joint member body, a plurality of wire guide protrusions each having a wire guide hole formed on a side edge of the joint member body, a first connection protrusion formed on the side edge of the joint member body, and a second connection protrusion formed on an other side edge of the joint member body;

folding each of the plurality of wire guide protrusions with respect to the joint member body;

forming a joint member assembly by arranging the plurality of joint members in parallel and connecting adjacent joint members via respective connection protrusions;

bending the joint member assembly such that each of the plurality of joint members has a ring shape; and connecting opposite ends of each of the plurality of joint members to each other.

2. The method of claim 1, wherein the forming the plurality of joint members comprises a drawing process that forms the wire guide hole having a depth greater than a thickness of the sheet material.

3. The method of claim 2, wherein the drawing process and pressing process are integrated, and the opposite ends of each of the joint members are connected by welding.

4. The method of claim 1, further comprising, after forming the plurality of joint members, processing the wire guide holes such that an exit part of the wire guide hole has a chamfered shape.

5. The method of claim 1, wherein the forming the plurality of joint members is performed by a single pressing process.

6. The method of claim 1, wherein the forming the joint member assembly comprises rivet-connecting the connection protrusions of the adjacent joint members.

7. The method of claim 1, wherein the forming the plurality of joint members comprises forming two wire guide protrusions, a first connection protrusion and a second connection protrusions on the side edge of the joint member body, and forming a third connection protrusion and a fourth connection protrusion on the other side edge of the joint member body.

* * * * *